United States Patent
Imai et al.

[11] 3,953,211
[45] Apr. 27, 1976

[54] DYE DEVELOPER FOR DIFFUSION TRANSFER ELEMENTS

[75] Inventors: Shinichi Imai; Shinsaku Fujita; Yukio Maekawa; Seiki Sakanoue, all of Minami-ashigara, Japan

[73] Assignee: Fuji Photo Film Co., Ltd., Minami-ashigara, Japan

[22] Filed: Sept. 18, 1974

[21] Appl. No.: 507,160

[30] Foreign Application Priority Data
Sept. 18, 1973 Japan............................ 48-105236

[52] U.S. Cl............................... 96/73; 96/3; 96/29 D; 96/77; 96/99
[51] Int. Cl.$^2$..................... G03C 1/76; G03C 1/40; G03C 1/10; G03C 7/00
[58] Field of Search .............. 96/3, 29 D, 77, 99, 96/73

[56] References Cited
UNITED STATES PATENTS

| | | | |
|---|---|---|---|
| 3,255,001 | 6/1966 | Blout et al. | 96/3 |
| 3,297,441 | 1/1967 | Green et al. | 96/3 |
| 3,312,682 | 4/1967 | Simon et al. | 96/3 |

*Primary Examiner*—David Klein
*Assistant Examiner*—Richard L. Schilling
*Attorney, Agent, or Firm*—Sughrue, Rothwell, Mion, Zinn & Macpeak

[57] ABSTRACT

A color diffusion transfer photographic light-sensitive material which comprises a support having thereon at least one light-sensitive silver halide emulsion layer containing a silver halide combined with a dye developer, one of the light-sensitive silver halide emulsion layers being combined with a dye developer represented by the following General Formula (I);

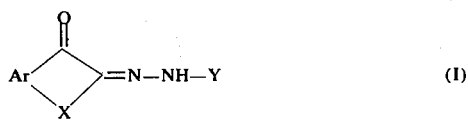

wherein Ar represents a divalent aromatic group; X represents

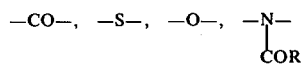

with R being an alkyl group having 1 to 3 carbon atoms, —NHCO— with the nitrogen atom being connected to the Ar group or —OCO— with the oxygen atom being connected to the Ar group; and Y represents an aromatic group having a substituent containing a hydroquinonyl group.

10 Claims, 2 Drawing Figures

DYE DEVELOPER FOR DIFFUSION TRANSFER ELEMENTS

BACKGROUND OF THE INVENTION

1. Field of the Invention

The present invention relates to a color diffusion transfer photographic light-sensitive material and, more particularly, it relates to a color diffusion transfer photographic light-sensitive material containing a novel dye developer.

2. Description of the Prior Art

Using a dye developer to obtain a diffusion transfer image is known. A dye developer is a dye which possesses in the dye molecule a group capable of developing exposed silver halide. A typical example of such a group capable of developing exposed silver halide is a hydroquinonyl group. This dye developer is soluble in an alkali solution but, upon being oxidized through the development of the exposed silver halide, it becomes alkali solution-insoluble.

The principle of obtaining diffusion transfer images using such a dye developer is as follows. That is, when a dye developer-containing silver halide light-sensitive material is processed, after imagewise exposure, with an alkali-containing processing solution to thereby develop the silver halide in the negative material with the dye developer, the dye developer located at the exposed areas becomes insoluble upon development of the silver halide, while the dye developer located at the unexposed areas remains alkali solution-soluble. Therefore, when a positive material having a dye-receiving layer is superposed on the negative material, the alkali solution-soluble dye developer migrates into the positive layer to form a positive image.

Therefore, in order to obtain faithful color reproduction of the transferred images, the dye developers to be transferred must have excellent absorbance characteristics. That is, in reproducing natural color by the combination of three dye developers which respectively absorb the three primary colors of blue, green and red, too much overlap of the absorption curves of the respective three dyes is not preferable and, conversely, too large a gap (separation) of the absorption curves is not preferable, either. In other words, it is desirable that the absorption curve shows an absorption maximum at a certain desirable wavelength and shows a sharp drop as the wavelength shifts to the side of the adjacent absorption curve of the other dye.

With a yellow dye, poor visual sensitivity results with an absorption maximum at a wavelength which is too short, while the images are reddish with an absorption maximum at a wavelength which is too long.

SUMMARY OF THE INVENTION

As a result of extensive investigations to obtain a yellow dye developer having the above-described hue, the present invention has been achieved. That is, the present invention provides a color diffusion transfer photographic light-sensitive material which comprises a support having thereon at least one light-sensitive silver halide emulsion layer containing a silver halide combined with a dye developer, one of the light-sensitive silver halide emulsion layers being combined with a dye developer represented by the following General Formula (I);

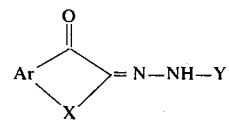

wherein Ar represents a divalent aromatic group; X represents

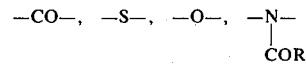

with R being an alkyl group having 1 to 3 carbon atoms, —NHCO— with the nitrogen atom being connected to the Ar group or —OCO— with the oxygen atom being connected to the Ar group; and Y represents an aromatic group having a substituent containing a hydroquinonyl group.

DETAILED DESCRIPTION OF THE INVENTION

Figure 1:
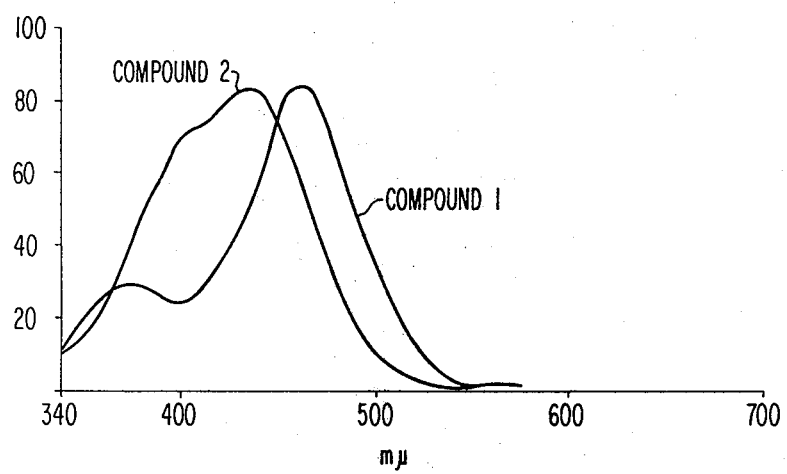
FIGS. 1 and 2 show the absorption spectra of yellow dye images obtained using color diffusion transfer photographic light-sensitive materials of the present invention.

The compounds represented by the above-illustrated General Formula (I) exist as a tautomer of compounds represented by the following General Formula (II);

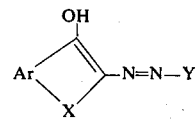

and hence they can be classified as azo dyes. In the present invention, however, they are designated "hydrazone-type compounds" represented by the aforesaid General Formula (I) since hydrazone-type is predominant.

In the above-described General Formula (I), specific examples of Ar include, e.g., an o-phenylene group, a methyl-substituted o-phenylene group, a chloro-substituted o-phenylene group, a methoxy-substituted o-phenylene group, etc. As the aromatic nucleus, those nuclei which are substituted with a halogen atom (for example, with a chlorine atom, a bromine atom, etc., being preferred), a lower alkyl group having 1 to 3 carbon atoms (e.g., a methyl group, an ethyl group, a propyl group, an isopropyl group, etc.), a lower alkoxy group having 1 to 3 carbon atoms (e.g., a methoxy group, an ethoxy group, a propoxy group, an isopropoxy group, etc.), or a like substituent are also included.

Specific examples of R in the General Formula (I) include, e.g., a methyl group, an ethyl group, a propyl group, an isopropyl group, etc.

In the Y group having a substituent containing a hydroquinonyl group (i.e., a 2,5-dihydroxyphenyl group), the hydroquinonyl group is preferably connected to the aromatic group through a divalent organic group, with the general formula —Ar—Z—Q, wherein Ar is as defined above, Z is a divalent organic group and Q is a hydroquinonyl group. The divalent group for Z is an alkylene group (for example, with a methylene group, an ethylene group, a trimethylene group, a propylene group, a tetramethylene group, etc., being preferred). Furthermore, the aromatic nucleus in Y includes those nuclei which are substituted with a halogen atom (for example, with a chlorine atom, a bromine atom, etc., being preferred), a lower alkyl group having 1 to 3 carbon atoms (e.g., a methyl group, an ethyl group, a propyl group, an isopropyl group, etc.), a lower alkoxy group having 1 to 3 carbon atoms (e.g., a methoxy group, an ethoxy group, a propoxy group, an isopropoxy group, etc.) or a like substituent.

Specific examples of the components represented by the aforesaid General Formula (I) are illustrated below.

(1) 2-[p-($\beta$-Hydroquinonylethyl)phenyl]hydrazono-3-oxo-1-thiaindane
(2) 2-[p-($\beta$-Hydroquinonylethyl)phenyl]hydrazono-1,3-dioxoindane
(3) 3-[p-($\beta$-Hydroquinonylethyl)phenyl]hydrazono-2,4-dioxo-1,2,3,4-tetrahydroquinoline
(4) 3-[m-(Hydroquinonylmethyl)phenyl]hydrazono-2,4-dioxochroman
(5) 3-[p-($\beta$-Hydroquinonylethyl)phenyl]hydrazono-6-methyl-2,4-dioxochroman
(6) 3-[p-($\beta$-Hydroquinonylethyl)phenyl]hydrazono-6-chloro-2,4-dioxochroman
(7) 2-(5-Hydroquinonylmethyl-2-methylphenyl)hydrazono-5-methoxy-3-oxocoumaran
(8) 2-[m-Chloro-p-($\beta$-hydroquinonylethyl)phenyl]hydrazono-1-acetyl-3-oxoindoline
(9) 2-[m-(Hydroquinonylmethyl)phenyl]hydrazono-3-oxo-1-thiaindane
(10) 2-[m-(N-Hydroquinonylmethyl-N-ethylcarbamoyl)-phenyl]hydrazono-1,3-dioxoindane
(11) 3-[m-(Hydroquinonylmethyl)phenyl]hydrazono-2,4-dioxochroman The compounds represented by the above General Formula (I) can be prepared, e.g., according to the process described in U.S. Pat. No. 3,134,672 or according to the process described in U.S. Pat. application Ser. No. 452,576, filed Mar. 19, 1974, by reacting both nitrous acid and an oxidizing agent with an aromatic primary amine having a hydroquinone residue in the molecule to obtain a diazonium salt having a quinone residue in the molecule, coupling the resulting diazonium salt with a compound represented by the following General Formula (III) to form an azo dye having a quinone residue in the molecule and reducing the resulting dye.

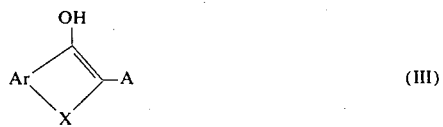

wherein Ar and X are the same as defined for General Formula (I), and A represents a hydrogen atom or a carboxy group.

Examples of the synthesis of dye developers of the present invention are illustrated below. Unless otherwise indicated herein, all parts, percents, ratios and the like are by weight.

SYNTHESIS EXAMPLE 1

Synthesis of Compound (1)

28 g of 4-(2,5-diacetoxyphenylethyl)aniline hydrochloride (described in U.S. Pat. No. 3,134,672) was dissolved in 600 ml of water and 16 ml of a 35% hydrochloric acid aqueous solution was added thereto. While maintaining the solution at a temperature not higher than 0°C under stirring, an aqueous solution prepared by dissolving 6.6 g of sodium nitrite in 50 ml of water was added dropwise thereto. After the dropwise addition, the mixture was stirred for 10 minutes and then neutralized to a pH of 5–7 using sodium acetate. Separately, 14 g of thioindoxyl-2-carboxylic acid was dissolved in 600 ml of ethanol and cooled. To this solution was added dropwise the above described diazonium solution. The crystals formed were collected and recrystallized from ethanol to obtain 12 g of a diacetoxy derivative having a melting point of 123°C. All of the product was dissolved in 120 ml of ethanol. Then, an alkali solution comprising 12 g of potassium hydroxide and 30 ml of water was added thereto and the mixture heated at 60°C for 10 minutes under reduced pressure. After cooling the mixture with ice, the mixture was neutralized with 60 ml of a 35 hydrochloric acid aqueous solution. The crystals formed were washed well with water and recrystallized from methanol to obtain 5 g of Compound (1) having a melting point of 245°–250°C.

SYNTHESIS EXAMPLE 2

Synthesis of Compound (2)

16.2 g of 4-(2,5-dihydroxyphenethyl)aniline, 54 ml of concentrated hydrochloric acid and 800 ml of ice-water were mixed, and 1.2 ml of 2-ethyl-1-hexanol was added thereto as a defoaming agent. This solution was cooled to a temperature lower than 0°C, and 100 ml of an aqueous solution containing 15.0 g of sodium nitrite was added dropwise thereto over a 2 minute period under stirring. After stirring the mixture for 90 minutes while maintaining the temperature at 0°C, 90 g of sodium acetate was added thereto. Then, a solution comprising 9.0 g of indane-1,3-dione, 2.4 g of sodium hydroxide, 120 ml of water and 900 ml of ethanol was poured into the above described diazonium solution. After stirring the solution for 3 hours, the crystals formed were collected by filtration and air-dried. The crystals were washed once with ethanol then twice with acetone, then collected by filtration and air-dried. Thus, 22 g of 4-(2-quinonylethyl)-phenylazo-1,3-indanedione having a decomposition point of 280°–283°C was obtained. 20 g of this quinone derivative was dissolved in 2 l of 1,2-dichloroethane, and 6 g of N,N-diethylhydroxylamine was added thereto. After stirring the mixture for two hours, the crystals precipitated were collected by filtration. Upon recrystallization from acetone, 12 g of Compound 2 having a melting point of 277°–280°C was obtained.

SYNTHESIS EXAMPLE 3

Synthesis of Compound (3)

In the same manner as in Synthesis Example 1, 17.6 g (0.05 mol) of a diazo compound of 4-(2,5-diacetoxyphenylethyl)-aniline hydrochloride was coupled with 2,4-dihydroxyquinoline monosodium salt tetrahydrate. Upon recrystallization of the product from acetone, 14 g of 2,4-dihydroxy-3-[4-(2,5-diacetoxyphenethyl)-phenylazo]quinoline was obtained. This was treated in the same manner as in Synthesis Example 1 using 60 ml of water, 120 ml of ethanol and 20 g of potassium hydroxide. After neutralization with a 35% hydrochloric acid aqueous solution, the crystals formed were collected by filtration, and washed well successively with water and acetone. Thus, 11.2 g of Compound 3 having a melting point of 293°–295°C was obtained.

SYNTHESIS EXAMPLE 4

Synthesis of Compound (5)

18 g of 4-hydroxy-6-methylcoumarin was diazo-coupled with 23.4 g of 2,4-dihydroxyphenethylaniline in the same manner as in Synthesis Example 2 to obtain 14 g of a quinone derivative. This product was refluxed in 1.6 l of 1,2-dichloroethane together with 4.6 g of N,N-diethylhydroxylamine. After one hour, the crystals precipitated were collected and recrystallized from ethanol. Thus, 10 g of Compound (5) having a melting point of 280°C was obtained.

The above-described dye developers are used in combination with light-sensitive silver halide emulsions to produce color diffusion transfer photographic light-sensitive materials.

In a color diffusion transfer photographic material using a dye developer, the combination of the color sensitivity of the silver halide emulsion and the spectral absorption of the dye developer is appropriately selected depending upon the intended color reproduction. In the reproduction of natural color according to subtractive color photography, a light-sensitive element having at least one combination of a silver halide emulsion having a selective spectral sensitivity in certain wavelength region with a compound having selective spectral absorption in the same wavelength region is used. In particular, a light-sensitive element comprising the combination of a blue-sensitive silver halide emulsion with a yellow dye developer, the combination of a green-sensitive silver halide emulsion with a magenta dye developer and the combination of a red-sensitive silver halide emulsion with a cyan dye developer is useful. These combination units of emulsions and dye developers are coated as adjacent layers or coated as one layer by forming each into particles and mixing. In a preferred multi-layered structure, a blue-sensitive silver halide emulsion, a green-sensitive silver halide emulsion and a red-sensitive silver halide emulsion are positioned, in sequence, from the side of exposure to incident light. In particular, in the case of high speed emulsions containing silver iodide, a yellow filter layer can be positioned between the blue-sensitive emulsion and the green-sensitive emulsion. This yellow filter layer can contain a yellow colloidal silver dispersion, an oil-soluble yellow dye dispersion, an acidic dye mordanted with a basic polymer, or a basic dye mordanted with an acidic polymer. The emulsion layers are advantageously separated from each other by an interlayer. The interlayer prevents undesired interactions from occurring between emulsion layer units having different color sensitivities. The interlayer can comprise a polymer containing fine pores formed by a latex of a hydrophilic polymer and hydrophobic polymer, as described in U.S. Pat. No. 3,625,685, or a polymer whose hydrophilicity is gradually increased by the processing composition, such as calcium alginate, as described in U.S. Pat. No. 3,384,483, as well as a hydrophilic polymer such as gelatin, polyacrylamide, a partially hydrolyzed product of polyvinyl acetate, etc.

The silver halide emulsion used in the present invention is a colloidal dispersion of silver chloride, silver bromide, silver chlorobromide, silver bromoiodide, silver chlorobromoiodide or a mixture thereof. The halide composition is selected depending upon the end-use purpose of the light-sensitive material and the processing conditions. In particular, a silver bromoiodide emulsion or a silver chlorobromoiodide emulsion containing about 1 mol % to 10 mol % iodide, not more than about 30 mol % chloride and the balance bromide is desirable. The silver halide grains used can be either a usual size or a fine size, but silver halide grains having a mean grain size of about 0.1 $\mu$ to about 2 $\mu$ are preferred. In some end-use purposes of the light-sensitive material, silver halides having a uniform grain size are preferred. The grains used can be in a cubic form, an octahedral form or a mixed crystal form. These silver halide emulsions can be prepared according to known conventional processes as described in P. G. Glafkides, *Chimie Photographique* 2nd. Ed. Chapters 18 to 23, Paul Montel, Paris (1957). That is, a soluble silver salt such as silver nitrate and a water-soluble halide such as potassium bromide are reacted with each other in the presence of a solution of a hydrophilic protective colloid such a as and crystals are allowed to develop in the presence of excess silver halide or a solvent for silver halide such as ammonia. As the silver halide precipitating method, a single or double jet method or a pAg-controlled double jet method can be employed. Removal of the soluble salts from the emulsion can be effected by washing and dialysis of the cool-set emulsion, by the combination of the addition of a sedimenting agent such as an anionic polymer having sulfone groups, sulfuric ester groups or carboxy groups or an anionic surface active agent and the adjustment of pH, or by the combination of the use of an acylated protein such as phthaloylated gelatin as a protective colloid and the adjustment of pH, to thereby cause sedimentation.

The silver halide emulsions used in the present invention are preferably subjected to chemical sensitization by a heat-treatment using the natural sensitizers contained in gelatin, a sulfur sensitizer such as sodium thiosulfate or N,N,N'-trimethylthiourea, a gold sensitizer such as a thiocyanate complex salt or thiosulfate complex salt of monovalent gold or a reducing sensitizer such as stannous chloride or hexamethylenetetramine, e.g., as disclosed in P. G. Glafkides, *Chimie Photographique* 2nd Edition, Paul Montel, Paris (1957). Also, emulsions which tend to form a latent image on the surface of the silver grains and emulsions which tend to form a latent image inside the silver halide grains as described in U.S. Pat. Nos. 2,592,550, 3,206,313, etc., can be used in the present invention.

The silver halide emulsions used in the present invention can be stabilized by additives such as 4-hydroxy-6-methyl-1,3,3a,7-tetrazaindene, 5-nitro 1-phenyl-58-chloromercuriquinoline, benzenesulfinic acid, pyrocatechin, 4-methyl-3-sulfoethylthiazolidine-2-thione, 4-phenyl-3-sulfoethylthiazolidine-2-thione, etc., e.g., as disclosed in C. E. K. Mees and T. H. James, *The Theory of the Photographic Process* 3rd Edition, Macmillan, New York. In addition, inorganic compounds such as cadmium salts, mercury salts, complex salts of platinum group metals such as the chloro complex salt of palladium, and the like, are also useful for stabilizing the light-sensitive material of the present invention. Furthermore, the silver halide emulsions used in the present invention can contain sensitizing compounds such as a polyethylene oxide compound.

The silver halide emulsions used in the present invention can possess, if desired, a color sensitivity expanded with spectral sensitizing dyes. Useful spectral sensitizing dyes include the cyanines, merocyanines, holopolar cyanines, styryls, hemicyanines, oxanols, hemioxanols, and the like. Specific examples of spectral sensitizing agents are described in P. Glafkides, supra, Chapters 35 to 41, and M. Hamer, *The Cyanine Dyes and Related Compounds* (Interscience). In particular, cyanines in which a nuclear nitrogen atom is substituted with an aliphatic group (e.g., an alkyl group, etc.) having a hydroxy group, a carboxy group or a sulfo group, e.g., those described in U.S. Pat. Nos. 2,503,776; 3,459,553 and 3,177,210, are especially useful for the practice of the present invention.

The dye developer used in the invention is generally dispersed in a carrier, a hydrophilic colloid, according to the following method. That is, a solution prepared by dissolving the dye developer in an organic solvent is added to a solution of a hydrophilic colloid and dispersed as fine droplets. Where a volatile solvent such as ethyl acetate, tetrahydrofuran, methyl ethyl ketone, etc., is used, the solvent can be removed during the drying of the photographic layers or according to the method described in U.S. Pat. Nos. 2,322,027 or 2,801,171. Where a water-soluble solvent such as dimethylformamide, 2-methoxyethanol, etc., is used, the solvent can be removed by washing according to the manner as described in U.S. Pat. Nos. 2,949,360; 3,396,027; etc. However, in order to stabilize the dispersion of the dye developer and to accelerate the dye image-forming step, it is advantageous to incorporate the dye developer in a solvent which is substantially insoluble in water and which has a boiling point of not less than about 200°C under ordinary pressure. Solvents suitable for this purpose include, e.g., dibutyl phthalate, tricresyl phosphate, trihexyl phosphate, N,N-diethyllauramide, etc. In order to accelerate dissolution of the dye developer, it is desirable to use the above described volatile or water-soluble solvents as auxiliary solvents.

Furthermore, oleophilic polymers can be used in place of or in addition to the high boiling solvent. In general, a colloid mill, a high pressure homogenizer, an ultrasonic emulsification apparatus or the like can be used to disperse the solution into a fine droplet form. As an emulsifying aid, mainly anionic surface active agents are advantageously used.

Suitable examples of supports which can be used include a cellulose nitrate film, a cellulose acetate film, a polyvinyl acetal film, a polystyrene film, a polyethylene terephthalate film, a polycarbonate film, etc. A suitable amount of silver halide which is coated on the support ranges from about 0.5 g/m² to 10 g/m². A suitable amount of dye developer can range from about 0.01 to 10 mol, preferably 0.05 to 0.5 mol, per mol of the silver halide.

The dye developer of the present invention is used as a yellow dye developer for a light-sensitive element.

To obtain multi-color images a magenta dye developer and a cyan dye developer, as disclosed in U.S. Pat. Nos. 3,134,672; 3,222,169; 3,255,001; etc., are used in combination with the yellow dye developer of the invention. Preferred dye developers include 5,8-dihydroxy-1,4-bis[(β-hydroquinonyl-α-methyl)-ethylamino]-anthraquinone, 1,4-bis-(2',5'-dihydroxyanilino)-anthraquinone, 1,4-bis[(β-hydroquinonyl-α-ethyl)ethylamino]-anthraquinone, 1-(β-hydroxy-α-ethyl-ethylamino)-4-(β-hydroquinonyl-α-methylethylamino)anthraquinone, etc., (cyan dye developers); and 4-isopropoxy-2-[p-(β-hydroquinonylethyl)-phenylazo]-1-naphthol, 1-acetoxy-2-[p-(β-hydroquinonylethyl)phenylazo]-4-methoxynaphthalene, 1-acetoxy-2-[p-(β-hydroquinonylethyl)-phenylazo]-4-propoxynaphthalene, 2-[p-(2',5'-dihydroxy-4'-methylphenethyl)-phenylazo]-4-propoxy-1-naphthol, etc., (magenta dye developers).

The light-sensitive element described above in detail is superposed on an image-receiving element (described hereinafter) in a face to face relationship and is processed, in general, by spreading an alkaline processing solution (described hereinafter) therebetween. The image-receiving element can be delaminated after transfer processing, if desired. Alternatively, as is described in U.S. Pat. No. 3,415,645, a transparent support can be used for the image-receiving layer and a reflecting layer is provided between the image-receiving layer and the light-sensitive layer, thus enabling the formed images to be seen without delamination of the image-receiving layer.

The image-receiving layer must contain a mordanting layer, such as a layer of a poly-4-vinylpyridine latex (particularly in polyvinyl alcohol), polyvinyl pyrrolidone, a quaternary ammonium salt-containing polymer as described in U.S. Pat. No. 3,239,337, etc. In addition, the image-receiving layer preferably possesses the function of neutralizing alkali brought into the layer from a processing composition. The processing composition contains alkali to provide a pH of higher than about 10, preferably higher than 11, which is high enough to accelerate the image-forming steps comprising the development of silver halide emulsion and the diffusion of the dye developer. After the substantial completion of the formation of the diffusion transferred images, the pH in the film unit is reduced to around neutrality, less than about 9, preferably less than 8, whereby further image-formation is actually discontinued to prevent the image tone from being changed with the lapse of time and to control discoloration and fading of the images and stain of the white background due to the high alkalinity. For this purpose, the film unit advantageously contains a neutralizing layer containing an acidic substance in a sufficient quantity to neutralize the alkali contained in the processing composition to the above described pH, that is, in an area concentration equivalent to or greater than the amount of alkali contained in the spread processing composition. Preferred acidic substances are those which contain an acidic group having a pKa of less than about 9, particularly, a carboxy group or a sulfonic acid group, or contains a precursor group capable of providing such an acidic group upon hydrolysis. More preferred examples include higher fatty acids such as oleic acid as described in U.S. Pat. No. 2,983,606, polymers of acrylic acid, methacrylic acid or maleic acid, the partially esterified polymers thereof, or acid anhydrides Specific examples of high molecular weight acidic substances are copolymers of a vinyl monomer (e.g., ethylene, vinyl acetate, vinyl methyl ether, etc.) and maleic anhydride, and the n-butyl half ester thereof; copolymer of butyl acrylate and acrylic acid; cellulose acetate hydrogen phthalate; and the like. In addition to these acidic substances, the neutralizing layer can contain polymers such as cellulose nitrate and polyvinyl acetate, and a plasticizer as described in U.S. Pat. No. 3,557,237. Furthermore, the neutralizing layer can be hardened through cross linking with a multi-functional aziridine compound, epoxy compound, etc. The neutralizing layer can be positioned in the image-receiving element and/or the light-sensitive element. In particular, the neutralizing layer is advantageously positioned between the support of the image-receiving element and the image-receiving layer. As is described in German Patent OLS No. 2,038,254, the acidic substances can be microencapsulated for incorporation in the film unit. A suitable thickness for the neutralizing layer ranges from about 10 to 50$\mu$.

The above described neutralizing layer or the acidic substance-containing layer is desirably separated from the spread processing composition layer by a neutralization rate-controlling layer. This neutralization rate-controlling layer functions to prevent an undesired reduction in the transfer image density due to a too fast reduction in pH before the necessary development of the silver halide emulsion layer and the formation of the diffusion transfer image are completed. That is, the neutralization rate-controlling layer functions to delay the reduction in pH until the necessary development and transfer are completed. In a preferable embodiment of the present invention, the image-receiving element possesses a multi-layered structure comprising a support—a neutralizing layer—a neutralization rate-controlling layer—a mordant layer (image-receiving layer) in this sequence. The neutralization rate-controlling layer comprises mainly polymers such as gelatin, polyvinyl alcohol, polyvinyl propyl ether, polyacrylamide, hydroxypropylmethyl cellulose, isopropyl cellulose, partially butyrated polyvinyl alcohol, partially hydrolyzed polyvinyl acetate, a copolymer of $\beta$-hydroxyethyl methacrylate and ethyl acrylate, and the like. These polymers are usefully hardened through cross linking with an aldehyde compound such as formaldehyde or a N-methylol compound. The neutralization rate-controlling layer preferably has a thickness of about 2 $\mu$ to 20 $\mu$.

On the other hand, the processing composition is a liquid composition containing processing components necessary for the development of the silver halide emulsion and necessary for the formation of the diffusion transfer dye image. The main solvent therein is water and, in some cases, a hydrophilic solvent such as methanol or 2-methoxyethanol can also be employed. The processing composition contains alkali in an amount sufficient to maintain the pH at a level necessary for causing development of the emulsion layer and to neutralize acids (e.g., hydrohalic acids such as hydrobromic acid, carboxylic acids such as acetic acid, and the like) produced during the various steps of development and dye image formation. As the alkali, there are used alkali metal hydroxides or salts or alkaline earth metal hydroxides or salts such as lithium hydroxide, sodium hydroxide, poassium hydroxide, calcium hydroxide dispersion, tetramethylammonium hydroxide, sodium carbonate, trisodium phosphate, amines such as diethylamine, etc. The processing composition preferably possesses a pH of not less than about 10, preferably not less than 12, at room temperature (about 20°–30°C). The processing composition also preferably contains a hydrophilic polymer such as high molecular weight polyvinyl alcohol, hydroxyethyl cellulose, sodium carboxymethyl cellulose or the like. These polymers impart to the processing composition a viscosity of not less than 1 poise, preferably about several hundred poise (500–600 poise) to about 1,000 poise, at room temperature, which not only facilitates the uniform spreading of the composition upon processing but also forms, upon concentration of the processing solution due to the migration of the aqueous solvent into the light-sensitive element and the image-receiving element in the course of the processing, an integral film, thus serving to unify the film unit after processing. In addition, this polymer film can serve, after the substantial completion of the formation of the diffusion transfer dye image, to control further migration of the coloring ingredients into the image-receiving layer, thereby preventing the image from being changed.

In some cases, the processing composition advantageously contains a light absorbent such as carbon black and a desensitizer as described in U.S. Pat. No. 3,579,333 so as to prevent the silver halide emulsion from being fogged by ambient light during processing.

In the color diffusion transfer method, development processing is desirably effected in the presence of an onium compound. Suitable examples of onium compounds include quaternary ammonium compounds, quaternary phosphonium compounds, and quaternary sulfonium compounds. Particularly useful compounds are, e.g., 1-benzyl-2-picolinium bromide, 1-(3-bromopropyl)-2-picolinium p-toluenesulfonate, 1-phenethyl-2-picolinium bromide, 2,4-dimethyl-1-phenethyl-pyridinium bromide, $\alpha$-picoline-$\beta$-naphthoylmethyl bromide, N,N-diethylpiperidinium bromide, phenethylphosphonium bromide, dodecyldimethylsulfonium p-toluenesulfonate, etc. These onium compounds are desirably incorporated in the alkaline processing composition. They are added, most preferably, in an amount of about 2 to 15 percent by weight based on the total weight of the processing composition. By effecting development processing in the presence of an onium compound, the image quality of the transferred images can be markedly enhanced. U.S. Pat. Nos. 3,411,904 and 3,173,786 describe, in detail, onium compounds other than those illustrated above and methods of using them. Furthermore, a restrainer such as benzotriazole can be incorporated in the processing composition.

The yellow dye developer used in the present invention is suitably used so that the molar ratio of the silver halide to the dye developer ranges from about 0.1 to 100. In particular, with a monochromatic color diffusion transfer photographic light-sensitive material for forming only a yellow dye image, the molar ratio of the silver halide to the yellow dye developer preferably ranges from about 4.1 to 8:1, while, with a color diffusion transfer photographic light-sensitive material for forming a multi-colored iamge, the molar ratio of the silver halide to the yellow dye developer preferably ranges from about 6:1 to 13.1.

The yellow dye image obtained by the color diffusion transfer photographic light-sensitive material of the present invention possesses an advantageous hue as will be clear from the following Examples. Therefore, faithful color reproduction is possible especially when the dye developer is used for the reproduction of multi-colored images.

The present invention is illustrated in greater detail by the following non-limiting examples of preferred embodiments of the present invention. Additionally, all percents, parts, ratios and the like are by weight unless otherwise specified.

EXAMPLE 1

A light-sensitive layer was prepared as follows.

2 g of Compound (1) was dissolved in a mixed solvent of 5 cc of N,N-diethyllaurylamide and 10 cc of methylcyclohexanone. This solution was then emulsified and dispersed in 30 cc of a 10% gelatin aqueous solution containing 2 cc of a 5% sodium n-dodecylbenzenesulfonate aqueous solution. After adding 2 cc of a 2% mucochloric acid aqueous solution to this emulsion, water was added thereto to make the total 100 cc. This emulsion solution was applied to a support of gelatin-subbed cellulose triacetate in a dry thickness of 3.5 $\mu$. On this layer was coated a mixture of 10 g of an emulsion and a silver bromoiodide emulsion containing $5.3 \times 10^{-2}$ mol of silver and 5.3 g of gelatin per 100 g of the emulsion in a dry thickness of 2 $\mu$, this emulsion being prepared by dissolving 1.0 g of 4'-methylphenylhydroquinone in a mixed solvent of 2 cc of N-n-butylacetanilide and 2 cc of ethyl acetate and emulsifying and dispersing the solution in 10 cc of a 10% gelatin aqueous solution containing 1 cc of a 5% sodium n-dodecylbenzenesulfonate aqueous solution. Furthermore, 100 cc of a 5% gelatin aqueous solution containing 1.5 cc of a 5% n-sodium dodecylbenzenesulfonate aqueous solution was coated thereon as a protective layer in a dry thickness of 1 $\mu$.

On the other hand, an image-receiving layer was prepared as follows.

On a transparent cellulose triacetate support was coated an aqueous solution containing a small amount of acetic acid and the following composition.

| | |
|---|---|
| Polyvinyl Alcohol (Gohsenol NH-18; made by Nippon Synthetic Chemical Industry Co., Ltd.) | 3 % |
| Poly-4-vinyl Pyridine | 3 % |

After imagewise exposure, the light-sensitive layer was superposed on an image-receiving layer and a processing solution having the following formulation was spread therebetween to effect development and transfer.

| | |
|---|---|
| Water | 100 cc |
| Potassium Hydroxide | 11.2 g |
| Hydroxyethyl Cellulose | 4.0 g |
| Benzotriazole | 3.5 g |
| Potassium Thiosulfate | 0.5 g |
| Lithium Nitrate | 0.5 g |
| Zinc Nitrate | 0.5 g |
| N-Benzyl-$\alpha$-picolinium Bromide | 2.3 g |

After development for about 1 minute, the image-receiving layer was delaminated. A yellow color image was transferred to the image-receiving layer in proportion to the exposure amount.

The absorption spectrum of this yellow color image is shown in FIG. 1. As is clear from this figure, it can be seen that the image possessed a hue desirable as a yellow color.

EXAMPLE 2

On a gelatin-subbed cellulose triacetate support were coated, in sequence, the following layers to provide a light-sensitive layer.

1. Cyan Dye Developer Layer 15 g of a cyan dye developer, 5,8-dihydroxy-1,4-bis-[($\beta$-$\alpha$-methyl)ethylamino]anthraquinone was dissolved in a mixed solution of 25 cc of N,N-diethyllaurylamide, 25 cc of methylcyclohexanone and 1 g of sodium diisooctyl-$\alpha$-sulfosuccinate under heating to 70°C. This solution was emulsified and dispersed in 160 cc of 10% aqueous solution containing 10 cc of a 5% sodium n-dodecylbenzenesulfonate aqueous solution, followed by adding water thereto to make the total 500 cc. Then, the resulting solution was coated in a dry thickness of 5 $\mu$.

2. Red-Sensitive Emulsion Layer

A red-sensitive silver bromoiodide emulsion containing $5.5 \times 10^{-2}$ mol of silver and 5.0 g of gelatin per 100 g of the emulsion (with 3,3',9-triethyl-5,5'-dichlorothiocarbocyanine iodide being used as a sensitizing dye) was coated in a dry thickness of 3.5 $\mu$.

3. Interlayer 100 cc of a 5% gelatin aqueous solution containing 1.5 cc of a 5% sodium n-dodecylbenzenesulfonate aqueous solution was coated in a dry thickness of 1.5 $\mu$.

4. Magenta Dye Developer Layer 10 g of a magenta dye developer, 4-isopropoxy-2-[p-($\beta$-hydroxyquinonylethyl)phenylazo]-1-naphthol was dissolved in a mixed solvent of 20 cc of N-n-butylacetanilide and 25 cc of methylcyclohexanone under heating to 70°C. This solution was emulsified and dispersed in 120 cc of a 10% gelatin aqueous solution containing 8 cc of a 5% sodium n-dodecylbenzenesulfonate aqueous solution, followed by adding water thereto to make the total 400 cc. Then, the resulting solution was coated in a dry thickness of 3.5 $\mu$.

5. Green-Sensitive Emulsion Layer

A green-sensitive silver bromoiodide emulsion containing $4.7 \times 10^{-2}$ mol of silver and 6.2 g of gelatin per 100 g of the emulsion (with 3,3',9-triethyl-5,5'-diphenyloxacarbocyanine bromide being used as a sensitizing dye) was coated in a dry thickness of 1.8 $\mu$.

6. Interlayer 100 cc of a 5% gelatin aqueous solution containing 1.5 cc of a 5% sodium n-dodecylbenzenesulfonate aqueous solution was coated in a dry thickness of 1.0 $\mu$.

7. Yellow Dye Developer Layer 10 g of a yellow dye developer (Compound (1)) was dissolved in a mixed solvent of 10 cc of N-n-butylacetanilide and 30 cc of cyclohexanone under heating to 70°C. This solution was emulsified and dispersed in 100 cc of a 10% gelatin aqueous solution containing 8 cc of a 5% sodium n-dodecylbenzenesulfonate aqueous solution. To this emulsion was added 5 cc of a 2% 2-hydroxy-4,6-dichloro-s-triazine aqueous solution. Then, water was added thereto to make the total 300 cc. This emulsion solution was coated in a dry thickness of 1.5 $\mu$.

8. Blue-Sensitive Emulsion Layer

A silver bromoiodide emulsion containing $3.5 \times 10^{-2}$ mol of silver and 6.5 g of gelatin per 100 g of the emulsion was coated in a dry thickness of 1.5 $\mu$.

9. Protective Layer 5 g of 4'-methylphenylhydroquinone was dissolved in a mixed solvent of 10 cc of tri-o-cresyl phosphate and 10 cc of ethyl acetate, and emulsified and dispersed in 10 cc of a 10% gelatin aqueous solution containing 2 cc of a 5% sodium n-dodecylbenzenesulfonate aqueous solution. 10 g of the thus obtained emulsion and 100 cc of a 5% gelatin aqueous solution containing 5 cc of a 2% mucochloric acid aqueous solution were coated in a dry thickness of 1 μ.

The light-sensitive layer was wedge exposed using blue light, followed by uniform, total exposure using a green light and a red light. After exposure, development and transfer were effected using the same image-receiving layer and the same processing solution as described in Example 1. Thus, a yellow color image was transferred to the image-receiving layer in proportion to the exposure amount.

As a result, a yellow color with a desirable hue was obtained.

EXAMPLE 3

A light-sensitive layer was prepared in the same manner as in Example 1 except for using 2 g of Compound (2) in lieu of Compound (1). This was imagewise exposed in the same manner as in Example 1, and superposed on an image-receiving layer. Then, a processing solution was spread therebetween to effect development and transfer. Thus, a yellow color image with a desirable hue was transferred into the image-receiving layer. The absorption spectrum of this dye image is shown in FIG. 1.

EXAMPLE 4

Figure 2:
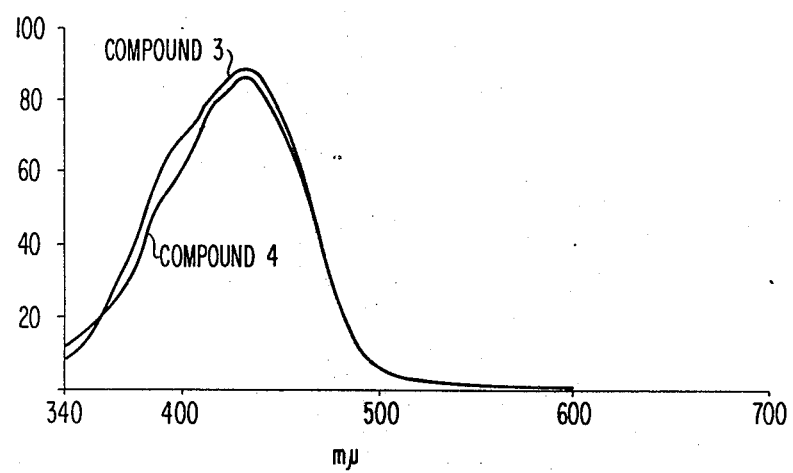

A light-sensitive layer was prepared in the same manner as in Example 1 except for using 2 g of Compound (3) in lieu of Compound (1), and then similarly processed. Thus, a yellow color image with a good hue was obtained in an image-receiving layer. The absorption spectrum of the dye image is shown in FIG. 2.

EXAMPLE 5

A light-sensitive layer was prepared in the same manner as in Example 1 except for using 2 g of Compound (4) in lieu of Compound (1), and then similarly processed. Thus, a yellow color image with a good hue was obtained in the image-receiving layer. The absorption spectrum of the dye image is shown in FIG. 2.

While the invention has been described in detail and with reference to specific embodiments thereof, it will be apparent to one skilled in the art that various changes and modifications can be made therein without departing from the spirit and scope thereof.

What is claimed is:

1. A color diffusion transfer photographic light-sensitive material which comprises a support having thereon at least one light-sensitive silver halide emulsion layer containing a silver halide combined with a dye developer, one of the light-sensitive silver halide emulsion layers being combined with a dye developer represented by the following General Formula (I);

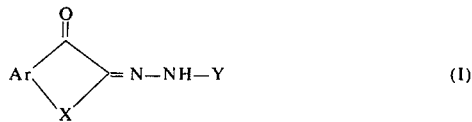

(I)

wherein Ar represents a phenylene group; X represents

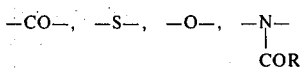

with R being an alkyl group having 1 to 3 carbon atoms, —NHCO— with the nitrogen atom being connected to the Ar group or —OCO— with the oxygen atom being connected to the Ar group; and Y represents an aromatic phenyl group with a hydroquinone attached thereto through an alkylene linkage.

2. The color diffusion transfer photographic light-sensitive material of Claim 1, wherein said phenylene group for Ar is a substituted phenylene group and wherein said aromatic phenyl group for Y is a substituted aromatic phenyl group.

3. The color diffusion transfer photographic light-sensitive material of Claim 1, wherein Ar is an o-phenylene group, a chloro-substituted o-phenylene group, a methyl-substituted o-phenylene group or a methoxy-substituted o-phenylene group.

4. The color diffusion transfer photographic light-sensitive material of Claim 1, wherein said compound of the General Formula (I) is 2-[p-(β-hydroquinonylethyl)phenyl]-hydrazono-3-oxo-1thiaindone, 2-[p-(β-hydroquinonylethyl)phenyl]-hydrazono-1,3-dioxoindane, 3-[p-(β-hydroquinonylethyl)phenyl]-hydrazono-2,4-dioxo-1,2,3,4tetrahydroquinoline, 3-[m-(hydroquinonylmethyl)phenyl]hydrazono-2,4-dioxochroman, 3-[p-β-hydroquinonylethyl)phenyl]hydrazono-6-methyl-2,4-dioxochroman, 3-[p-(β-hydroquinonylethyl)phenyl]hydrazono-6-chloro-2,4-dioxochroman, 2-(5-hydroquinonylmethyl-2-methylphenyl)hydrazono-5-methoxy-3-oxocoumaran, 2-[m-chloro-p-(β-hydroquinonylethyl)-phenyl]hydrazono-1-acetyl-3-oxoindoline, 2-[m-(hydroquinonlymethyl)phenyl]hydrazono-3-oxo-1-thiaindane, 2-[m-(N-hydroquinonyl-methyl-N-ethylcarbamoyl)phenyl]hydrazono-1,3-dioxoindane, or 3-[m-(hydroquinonylmethyl)pheny(]hydrazono-2,4-dioxochroman.

5. The color diffusion transfer photographic light-sensitive material of claim 1, wherein said material comprises a support having thereon in order a blue-sensitive silver halide emulsion layer in combination with a yellow dye developer, a green-sensitive silver halide emulsion layer in combination with a magenta dye developer, and a red-sensitive silver halide emulsion layer in combination with a cyan dry developer.

6. A color diffusion transfer photographic unit comprising a light-sensitive element comprising the color diffusion transfer photographic light-sensitive material of claim 1, and an image receiving element comprising a support having thereon, in order, a neutralizing layer, a neutralizing rate-controlling layer and an image-receiving layer for receiving the transferred dye image from said light-sensitive element.

7. The color diffusion transfer photographic light-sensitive material of claim 2, wherein R represents a methyl group, an ethyl group, a propyl group or an iso-propyl group.

8. The color diffusion transfer photographic light-sensitive material of claim 2, wherein said substituent contained in said phenylene group of Ar is a chlorine atom, a bromine atom, a methyl group, an ethyl group, a propyl group, an isopropyl group, a methoxy group, an ethoxy group, a propoxy group or an isopropoxy group and wherein said substituent of said substituted aromatic phenyl group of Y is a chlorine atom, a bromine atom, a methyl group, an ethyl group, a propyl group, an isopropyl group, a methoxy group, an ethoxy group, a propoxy group, or an iso-propoxy group.

9. The color diffusion transfer photographic light-sensitive material of claim 1, wherein said alkylene linkage of Y is a methylene group, an ethylene group, a trimethylene group, a propylene group or a tetramethylene group.

10. The color diffusion transfer photographic light-sensitive material of claim 8, wherein said alkylene linkage of Y is a methylene group, an ethylene group, a trimethylene group, a propylene group or a tetramethylene group.

* * * * *